(12) United States Patent
Strominger et al.

(10) Patent No.: US 9,909,219 B2
(45) Date of Patent: Mar. 6, 2018

(54) SLURRY BIOCIDE

(71) Applicant: ECOLAB USA INC., St. Paul, MN (US)

(72) Inventors: Michael G. Strominger, Naperville, IL (US); Danilo Zim, Campinas (BR); Fabiane Cássia de Sá Aureliano, Campinas (BR)

(73) Assignee: Ecolab USA Inc., St Paul, MN (US)

( * ) Notice: Subject to any disclaimer, the term of this patent is extended or adjusted under 35 U.S.C. 154(b) by 24 days.

(21) Appl. No.: 14/252,709

(22) Filed: Apr. 14, 2014

(65) Prior Publication Data

US 2015/0291462 A1    Oct. 15, 2015

(51) Int. Cl.
| | |
|---|---|
| A01N 59/00 | (2006.01) |
| C02F 1/50 | (2006.01) |
| C02F 1/72 | (2006.01) |
| C02F 1/76 | (2006.01) |
| C23F 11/10 | (2006.01) |

(Continued)

(52) U.S. Cl.
CPC .............. *C23F 11/10* (2013.01); *A01N 59/00* (2013.01); *C23F 11/143* (2013.01); *C23F 11/163* (2013.01); *C23F 11/188* (2013.01); *C02F 1/50* (2013.01); *C02F 1/722* (2013.01); *C02F 1/76* (2013.01); *C02F 1/766* (2013.01);

(Continued)

(58) Field of Classification Search
CPC .... C02F 1/50; C02F 1/72; C02F 1/722; C02F 1/76; C02F 1/766; C02F 9/00; C02F 5/08; C02F 2103/08; C02F 2103/10; C02F 2103/34; C02F 2303/08; C02F 2303/20; C02F 2303/22; C02F 2307/14; A01N 59/00; C23F 11/10; C23F 11/143; C23F 11/163; C23F 11/188
See application file for complete search history.

(56) References Cited

U.S. PATENT DOCUMENTS

| 4,206,610 A | 6/1980 | Santhanam |
| 4,282,006 A | 8/1981 | Funk |

(Continued)

FOREIGN PATENT DOCUMENTS

| WO | 96/14092 | 5/1996 |
| WO | WO 1996033296 | 10/1996 |
| WO | 2012/134790 | 10/2012 |

OTHER PUBLICATIONS

J. W. Costerton, et al., Influence of biofilm on efficacy of biocides on corrosion-causing bacteria, Materials Performance, vol. 23, No. 2, p. 13, (1984).

(Continued)

*Primary Examiner* — Lucas Stelling
(74) *Attorney, Agent, or Firm* — Kagan Binder, PLLC (57) ABSTRACT

The invention provides methods and compositions for addressing the problem of microorganism infestations and especially biocorrosion in slurry transporting pipelines. The method comprises treating pipeline fluid (especially plug fluid) with an oxidizing biocide in an amount higher than the oxidant demand of the pipeline and a non-oxidizing biocide in an amount less than 30% of the minimum necessary to sterilize the microbiological organisms. This treatment makes use of the unique characteristics of a slurry pipeline to eliminate microorganisms without harming the pipeline as would be expected by using an oxidizing biocide.

18 Claims, 3 Drawing Sheets

(51) Int. Cl.
*C23F 11/14* (2006.01)
*C23F 11/16* (2006.01)
*C23F 11/18* (2006.01)

(52) U.S. Cl.
CPC ...... *C02F 2303/04* (2013.01); *C02F 2303/08* (2013.01); *C02F 2303/20* (2013.01)

(56) References Cited

U.S. PATENT DOCUMENTS

| | | | |
|---|---|---|---|
| 4,297,224 A * | 10/1981 | Macchiarolo | C02F 1/50 210/755 |
| 4,546,612 A | 10/1985 | Santhanam | |
| 4,624,680 A | 11/1986 | Funk | |
| 4,855,296 A | 8/1989 | Donofrio et al. | |
| 5,300,235 A * | 4/1994 | Clewlow | C23F 11/145 208/47 |
| 5,368,749 A | 11/1994 | La Zonby | |
| 5,709,731 A | 1/1998 | Armstrong | |
| 5,753,180 A * | 5/1998 | Burger | C23F 11/122 134/42 |
| 6,586,497 B2 | 7/2003 | Gay et al. | |
| 8,168,071 B2 | 5/2012 | Hann | |
| 8,557,338 B1 | 10/2013 | Zirn et al. | |
| 2003/0012605 A1 | 1/2003 | Miller et al. | |
| 2004/0035803 A1 | 2/2004 | Cronan, Jr. et al. | |
| 2004/0129644 A1 | 7/2004 | Unhoch et al. | |
| 2006/0049119 A1 | 3/2006 | Ludensky et al. | |
| 2006/0231505 A1 * | 10/2006 | Mayer | C02F 1/76 210/764 |
| 2007/0045199 A1 | 3/2007 | Mayer et al. | |
| 2009/0107923 A1 | 4/2009 | Barak et al. | |

OTHER PUBLICATIONS

International Search Report for International Application No. PCT/US2015/022783, dated May 29, 2015, 3 pages.
Written Opinion for International Application No. PCT/US2015/022783, dated May 29, 2015, 5 pages.
International Search Report and Written Opinion for European Application No. 15779397.7 dated Dec. 7, 2017 (11 pages).

* cited by examiner

SLURRY BIOCIDE

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

This invention relates generally to novel methods, apparatuses, and compositions of matter useful in controlling the growth of organisms within slurry transporting pipelines. As described for example in U.S. Pat. Nos. 8,168,071, 6,586,497, 5,709,731, 4,624,680, 4,546,612, 4,282,006 and 4,206,610, the transport of many slurries (such as ore slurries) is commonly accomplished using mild steel pipelines. Essentially, the ore is grinded and mixed with a fluid like water in order to form a mud that can then be pumped through the pipeline.

As with any system comprising large volumes of water, uncontrolled microbial growth and activity can create severe operational, environmental, and human safety problems in slurry pipelines. Problems caused or intensified by microbial growth and activity includes corrosion, solids production, hydrogen sulfide ($H_2S$) generation, and contamination of the slurry. The microorganisms responsible for these problems can be both aerobic and anaerobic and include oxygen-reducing and sulfate-reducing bacteria. As the slurry water often comprises reservoir or seawater it will typically contain both problematic bacteria as well as required nutrients.

As described in International Patent application WO 1996033296, bacterial corrosion is often caused by sessile anaerobic bacteria living under a thick biofilm composed of aerobic and facultative bacteria enmeshed in a fibrous anionic ion exchange resin that severely limits the penetration of charged molecules. (See *Influence of biofilm on efficacy of biocides on corrosion-causing bacteria*, by J. W. Costerton, et al, Materials Performance, Vol. 23, No. 2, p. 13, (1984)). Corrosion (pitting) caused by bacteria frequently results in extensive damage. Pipe systems, tank bottoms, and other pieces of equipment can rapidly fail if there are areas where microbial corrosion is occurring.

A number of prior art methods have been proposed for addressing microbiological infestations of pipelines which include: temperature control, metabolite removal, pH control, Eh control, radiation, filtration, salinity control, chemical control (e.g., oxidizers, biocides, acids, alkalis), solids control (e.g., pigging or scraping the internal pipeline), and bacteriological controls (e.g., bacteria phages, enzymes, parasitic bacteria, monoclonal antibodies, competitive microflora). Some of these methods will kill the microorganisms, while others stress or disturb them sufficiently to inhibit their activity. Unfortunately none of these methods present many downsides. Moreover, they are not optimized for the specific conditions and requirements inherent in infestations within slurry transporting pipelines.

Accordingly, there is an ongoing need for a method of reducing microbiological infestations within slurry transporting pipelines. The art described in this section is not intended to constitute an admission that any patent, publication or other information referred to herein is "Prior Art" with respect to this invention, unless specifically designated as such. In addition, this section should not be construed to mean that a search has been made or that no other pertinent information as defined in 37 CFR §1.56(a) exists.

BRIEF SUMMARY OF THE INVENTION

To satisfy the long-felt but unsolved needs identified above, at least one embodiment of the invention is directed towards a method of reducing the presence of microorganisms from a slurry transporting pipeline. The method comprises the steps of: adding an oxidizing biocide to a fluid in an amount higher than the oxidant demand of the pipeline, adding a non-oxidizing biocide to a fluid in an amount less than 30% of the minimum necessary to sterilize the microbiological organisms present before the oxidizing biocide was added, and feeding the fluid into the pipeline.

The fluid may enter the pipeline after the biocides have been added. The fluid may be a plug, river water, freshwater, and/or seawater. The oxidizing biocide may be one selected from the list consisting of: chlorine dioxide, chlorine gas, hypochlorous acid, bromine derived biocides, and any combination thereof. The oxidizing biocide may be a reaction product of metal chlorate, hydrogen peroxide, and an acid selected from mineral acid, chlorous acid, and any combination thereof. The method may further comprise adding a corrosion inhibitor to the fluid, wherein but for the presence of the non-oxidizing biocide, the corrosion inhibitor would have been rendered ineffective by the oxidizing biocide. The pipeline may suffer no more corrosion-erosion than it would have had the corrosion inhibitor been added to the fluid in the absence of the oxidizing biocide and/or the non-oxidizing biocide.

At least a portion of the pipeline in contact with the fluid may be constructed essentially out of mild steel and the presence of the oxidizing biocide reduces biocorrosion and substantially does not cause corrosion. The dosage of the biocides may be such that it reduces biocorrosion at the distal end of the pipeline while substantially not increasing corrosion at the proximal end of the pipeline. The dosage of oxidizing biocide to the fluid may be 1-10 ppm and the dosage of non-oxidizing biocide to the fluid may be 1-200 ppm more preferably between 50-120 ppm. The majority of the pipeline may be in contact with the fluid and/or may be constructed essentially out of mild steel and the presence of the oxidizing biocide reduces biocorrosion and does not cause corrosion. The method may exclude the presence of a nitrogenous bromine compound.

Additional features and advantages are described herein, and will be apparent from, the following Detailed Description.

BRIEF DESCRIPTION OF THE DRAWINGS

A detailed description of the invention is hereafter described with specific reference being made to the drawings in which.

For the purposes of this disclosure, like reference numerals in the figures shall refer to like features unless otherwise indicated. The drawings are only an exemplification of the principles of the invention and are not intended to limit the invention to the particular embodiments illustrated.

DETAILED DESCRIPTION OF THE INVENTION

Definitions

The following definitions are provided to determine how terms used in this application, and in particular how the claims, are to be construed. The organization of the definitions is for convenience only and is not intended to limit any of the definitions to any particular category.

"Comminuted" means powdered, pulverized, ground, or otherwise rendered into fine solid particles.

"Consisting Essentially of" means that the methods and compositions may include additional steps, components, ingredients or the like, but only if the additional steps, components and/or ingredients do not materially alter the basic and novel characteristics of the claimed methods and compositions.

"Biocorrosion" means corrosion resulting from the presence and activities of microorganisms which induce, accelerate, and/or maintain a corrosion reaction in a solid surface (such as metal)-fluid interface, typically conditioned by a biofilm, its rate and effects are influenced by the type/composition of the solid surface and/or fluid, the arrangement of the microorganisms on the solid surface, and/or the metabolic activity of the microorganisms.

"Corrosion" means a chemical process which takes place on the surface of the solid material in contact with a fluidic medium, the process causes a loss of material from the surface to the medium, it may be the result of an anodic-cathodic type reaction caused between iron and water, it excludes erosion type processes.

"Corrosion-Erosion" means a process in which both corrosion and erosion are occurring simultaneously, often corrosion-erosion results in a synergistic effect resulting in greater mass loss than the sum of the corrosion with the erosion expected for a given medium.

"Corrosion Inhibitor" means a composition of matter known in the art to inhibit the rate of corrosion on a surface in contact with a corrosive fluid.

"Erosion" means a physical abrasive process which takes place on the surface of the solid material in contact with a fluidic medium, the process causes a loss of material from the surface to the medium, and it excludes corrosion type processes.

"Hard" means the measure of how resistant a particular kind of solid matter is to various kinds of permanent shape change when a force is applied, hardness is generally characterized by strong intermolecular bonds, but the behavior of solid materials under force is complex; therefore, there are different measurements of hardness including: scratch hardness, indentation hardness, and rebound hardness.

"Microorganism" means any organism small enough to insinuate itself within, adjacent to, on top of, or attached to equipment used in or connected to a slurry transporting pipeline, it includes but is not limited to those organisms so small that they cannot be seen without the aid of a microscope, collections or colonies of such small organisms that can be seen by the naked eye but which comprise a number of individual organisms that are too small to be seen by the naked eye, as well as one or more organisms that can be seen by the naked eye, it includes but is not limited to any organism whose presence, in some way impairs the transport or value of the slurry, it also includes but is not limited to iron-oxidizing, sulfate reducing, and sulfur-oxidizing microorganisms.

"Mild Steel" means an iron alloy that contains less than 1.65% of manganese, less than 0.60% of silicon and less than 0.60% of copper, and has a carbon content of between 0.05% and 0.29%, mild steel includes steel alloys with no minimum amount of chromium, cobalt, molybdenum, nickel, niobium, titanium, tungsten, vanadium or zirconium, or any other element. Usually carbon content is between 0.05% and 0.29%. Mild steel undergoes more corrosion under such atmospheric conditions than when compared to stainless steel (which has for instance higher nickel and chromium content) does.

"Plug" means a fluid under flux in a slurry pipeline that is either substantially free of all but trace or residual amounts of slurry or suspended solids; plugs are sometimes used when it is desired to keep the pipeline under flux but also not pass slurry to the terminus of the pipeline, plug fluids may comprise but are not limited to one or more of: water, reservoir water, seawater, sewer water, lake water, cooling tower water, boiler water, make down water, wastewater, and water separated from slurry.

"Separation" means a mass transfer process that converts a mixture of substances into two or more distinct product mixtures, at least one of which is enriched in one or more of the mixture's constituents, it includes but is not limited to such processes as: Adsorption, Centrifugation, cyclonic separation, density based separation, Chromatography, Crystallization, Decantation, Distillation, Drying, Electrophoresis, Elutriation, Evaporation, Extraction, Leaching extraction, Liquid-liquid extraction, Solid phase extraction, Flotation, Dissolved air flotation, Froth flotation, Flocculation, Filtration, Mesh filtration, membrane filtration, microfiltration, ultrafiltration, nanofiltration, reverse osmosis, Fractional distillation, Fractional freezing, Magnetic separation, Precipitation, Recrystallization, Sedimentation, Gravity separation, Sieving, Stripping, Sublimation, Vapor-liquid separation, Winnowing, Zone refining, and any combination thereof.

"Slurry" means medium comprising a fluidic carrier within which is suspended a number of solid particles, the solid particles include but are not limited to ground rock such as ore, coal ore, bauxite, iron ore, and the like and the fluid is often a liquid such as water, the amount of solid is such that the fluidic carrier has properties associated with a fluid thicker than the carrier alone, slurries include but are not limited to dispersions, solutions, and can have liquid or water carrier fluids.

"Solids %" means the portion of an aqueous system by weight that is silica bearing particles of the continuous phase.

"Thickener" or "Settler" means a vessel used to effect a solid-liquid separation of a slurry, often with the addition of flocculants, the vessel constructed and arranged to receive a slurry, retain the slurry for a period of time sufficient to allow solid portions of the slurry to settle downward (underflow) away from a more liquid portion of the slurry (overflow), decant the overflow, and remove the underflow. Thickener underflow and thickener overflow are often passed on to filters to further separate solids from liquids.

"Under Flux" means a having a fluid (including but not limited to slurry fluid, liquid fluid, water, and any combination thereof) actively passing through a system such as a pipeline.

"Water Soluble" means materials that are soluble in water to at least 3%, by weight, at 25 degrees C.

In the event that the above definitions or a description stated elsewhere in this application is inconsistent with a meaning (explicit or implicit) which is commonly used, in a dictionary, or stated in a source incorporated by reference into this application, the application and the claim terms in particular are understood to be construed according to the definition or description in this application, and not according to the common definition, dictionary definition, or the definition that was incorporated by reference. In light of the above, in the event that a term can only be understood if it is construed by a dictionary, if the term is defined by the *Kirk-Othmer Encyclopedia of Chemical Technology*, 5th Edition, (2005), (Published by Wiley, John & Sons, Inc.) this definition shall control how the term is to be defined in the claims. All illustrated chemical structures also include all possible stereoisomer alternatives.

Embodiments

At least one embodiment of the invention is directed to a method which minimizes the infestation of one or more microorganisms within pipelines during ore slurry transport. For a number of reasons including to prevent the formation of plugs and blockages due to settling of suspended particles within a pipeline, and also to prevent expansion-contraction type fractures or deformations due to changes in pressure differentials, slurry transport pipelines are often kept under flux for large periods of time (sometimes substantially most or essentially all, of the time). This often results in the pipeline needing to remain under flux even after the pipeline terminus (such as a refinery or smelter) has absorbed the maximum amount of slurry it can (or its operator wishes to) handle. As a result in order to remain under flux, slurry pipelines are sometimes filled with plugs. Because by definition plugs are low value bulk materials that are often discarded after passage through the pipeline, plugs are often unclean and are a vector for introducing microorganisms into slurry pipelines.

In at least one embodiment a fluid is pre-treated to remove microorganisms before it is fed into a pipeline. The fluid may become plug fluid and/or slurry fluid. In at least one embodiment the pre-treatment is tailored for use in a pipeline. Problems innate to pipelines that differ from other industrial process streams result from the sheer distances that the fluid traverses. It is extremely difficult for a biocide to remain chemically active in a fluid after it has traveled tens, hundreds, possibly thousands of miles. As a result according to the prior art, either expensive biocide introduction systems must be located throughout the length of the pipeline and must utilize complicated equipment to coordinate the biocide feed with the pipeline fluid flow, or huge quantities of biocide must be introduced into the fluid.

Also, because of the long distances along which microorganisms are left undisturbed in the pipelines, pipeline inhabiting microorganisms are even more likely to develop/evolve resistance to many biocides than is normally the case in other process systems. This results in a need to use highly oxidizing biocides. Unfortunately because slurry transport pipelines are often largely or entirely made out of mild steel, effective oxidizing biocides will readily corrode them. Such corrosion is especially problematic in slurry pipelines because when combined with the innate erosion caused by hard solids in the slurry such as iron or bauxite, devastatingly destructive corrosion-erosion may occur. In addition, highly oxidizing biocides are themselves so reactive as to lose their chemical activity shortly after introduction into the pipeline.

As a result the prior art leaves users with an unacceptable tradeoff; the pipeline operator must either accept excessive microorganism infestation or excessive pipe corrosion. Even worse the operator may have to make a tradeoff between protecting different portions of the pipeline. For example, adding sufficient oxidizing biocide that is still active when it reaches a more distal (such as by the terminus) point of the pipeline can only be accomplished by dosing concentrations highly corrosive to a more proximal (such as by the fluid entry point) point. Conversely using safer dosages at a more proximal point of the pipeline will result in a wholly ineffective biocide when it reaches a far off more distal point. Fortunately the invention offers a way for operators to escape this unacceptable trade off.

In at least one embodiment the fluid is treated in a manner that both prevents microorganism infestation and does not corrode (or excessively corrode) the pipeline. The method may involve: treating the fluid with an oxidizing biocide, treating the fluid with a non-oxidizing biocide after the oxidizing biocide, and feeding the fluid into a slurry transport pipeline.

The amount of oxidizing biocide may be sufficient to eliminate substantially all of the microorganisms in the fluid. The amount of non-oxidizing biocide may be in an amount sufficient to neutralize the oxidizing biocide but insufficient to eliminate substantially most of the microorganisms that had previously been in the fluid. The non-oxidizing biocide may prevent any further contamination while the plug of water is pumped through the pipeline.

Biocides are often classified as oxidizing or non-oxidizing, depending on their chemical composition and mode of action. Typically when oxidizing biocides are used in microbiological control programs in other process systems they are applied in such a manner as to apply quantities sufficient to maintain a free oxidizer residual in the process. This can be problematic in process liquids in slurry transport pipelines because they contain high concentrations of dissolved and particulate inorganic and organic materials. Such process waters exhibit a high and variable "demand" on the oxidizer (i.e., the oxidizer can react with the inorganic and organic materials and be rendered ineffective as a biocide). Also, the excess of oxidizing biocide could corrode the mild steel pipeline making the treatment pointless.

For example, oxidizing biocides are consumed by inorganic species such as ferrous iron, reduced manganese, sulfides, sulfites, etc. as well as organic compounds such cellulosic fibers and additives. As slurry transport pipelines commonly carry such items and/or elute them from erosion and/or corrosion of the mild steel pipes, these pipelines are especially inhospitable to oxidizing biocides due to high "demand". As described for example in U.S. Pat. Nos. 7,052,614, 4,872,999 and 6,132,628, such demand might be countered by the addition of oxidizer stabilizers such as nitrogenous bromine compounds. At least one embodiment includes the presence of oxidizer stabilizers including but not limited to nitrogenous bromine compounds. At least one embodiment excludes the presence of oxidizer stabilizers including but not limited to nitrogenous bromine compounds.

Non-oxidizing biocide useful in the invention include, but are not limited to, aldehydes, formaldehyde releasing compounds, halogenated hydrocarbons, phenolics, amides, halogenated amides, carbamates, heterocyclic compounds containing nitrogen and sulfur atoms in the ring structure, electrophilic active substances having an activated halogen group in the α-position and/or in the vinyl position to an electronegative group, nucleophilic active substance having an alkyl group and at least one leaving group, and surface active agents. The aldehyde containing compounds can be linear, branched or aromatic. An example of aldehyde useful in the invention, but is not limited to, glutaraldehyde. The formaldehyde releasing compounds are preferably halogenated, methylated nitro-hydrocarbons, for example 2-bromo-2-nitro-propane-1,3-diol (Bronopol). The amides are preferably halogenated, for example 2,2-dibromo-3-nitrilopropionamide (DBNPA). The heterocyclic compounds useful in the invention include thiazole and isothiazolinone derivatives. Some examples of heterocyclic compounds include, but are not limited to, 5-chloro-2-methyl-4-isothiazolin-3-one (CMIT) and 2-methyl-4-isothiazolin-3-one (MIT). The surface active agents useful in the invention include detergents, wetting agents and emulsifiers. Some examples of surface active agents include, but are not limited to, long chain quaternary ammonium compounds, aliphatic diamines, guanidines and biguanidines.

Additional examples of the non-oxidizing biocide useful in the invention include, but are not limited to, 2-methyl-4-isothiazolin-3-one (MIT); 5-chloro-2-methyl-4-isothiazolin-3-one (CMIT); 2-n-octyl-4-isothiazolin-3-one; 4,5-dichloro-2-(n-octyl)-4-isothiazolin-3-one; 1,2-benziosthiazolin-3-one; glutaraldehyde; orfΛo-phthalaldehyde; 2,2-dibromo-3-nitrilopropionamide (DBNPA); 2-bromo-2-nitrostyrene, 2-nitrostyrene; 2-bromo-4'-hydroxyacetophenone; methylene bisthiocyanate (MBT); 2-(thiocyanomethylthio)benzothiazole; 3-iodopropynyl-Λ/-butylcarbamate; n-alkyl dimethyl benzyl ammonium chloride; didecyl dimethyl ammonium chloride; alkenyl dimethylethyl ammonium chloride; 4,5-dichloro-1,2-dithiol-3-one; decylthioethylamine; 2-bromo-2-nitropropane-1,3-diol; π-dodecylguanidine hydrochloride; n-dodecylguanidine acetate; 1-(3-chloroallyl)-3,5,7-triaza-1-azoniaadamantane chloride; 1,2-dibromo-2,4-dicyanobutane; bis(1,4-bromoacetoxy)-2-butene; bis(1,2-bromoacetoxy)ethane; bis(trichloromethyl) sulfone; diiodomethyl-p-tolylsulfone; sodium orfΛo-phenylphenate; tetrahydro-3,5-dimethyl-2H-1,3,5-hydrazine-2-thione; cationic salts of dithiocarbamate derivatives; 4-chloro-3-methyl-phenol; 2,4,4'-trichloro-2'-hydroxy-diphenylether; and poly(oxyethylene(dimethyliminio)ethylene(dimethyliminio)ethylene dichloride.

In at least one embodiment the oxidizing biocide and/or the method of its introduction is one or more of those described in one or more of U.S. Pat. Nos. 5,895,638, 6,387,344, 7,070,710, 6,790,427, and 7,682,592. In at least one embodiment the oxidizing biocide is and/or comprises chlorine dioxide, chlorine gas, hypochlorous acid, bromine derived biocides, and any combination thereof. Chlorine dioxide may be produced by prior (before introduction to the fluid) or in situ (within the fluid) reduction of chlorate ions with a peroxide (such as hydrogen peroxide) in the presence of an acid (such as but not limited to sulfuric acid and/or hydrochloric acid). The chlorate ions may be derived from metal chlorates. The oxidizing biocide may further comprise one or more of: a protective colloid, a radical scavenger, and/or a complexing agent. The ratio of chlorate to peroxide may range from 1:10 to 10:1.

In at least one embodiment the oxidizing biocide is dosed into the fluid in an amount that is sufficient to sterilize the fluid. For example this may be 1-50 ppm oxidant (for example 1-50 ppm chlorine dioxide). The non-oxidizing biocide is then dosed in an amount of 1%-30% of the amount needed to sterilize the fluid (many non-oxidizing biocides sterilize at 500-350 ppm so the dosage may be as low as 5-200 more preferably 5-120 ppm or more or less).

In at least one embodiment the non-oxidizing biocide is added: 1) to prevent further contaminations, 2) to eliminate all traces of the oxidazing biocide and therefore prevent corrosion, and/or 3) to exterminate any microorganism already within the pipeline. The non-oxidizing biocide may eventually eliminate a few microorganisms that somehow have survived the oxidizing biocide but this is not its primary function.

Without being limited by a particular theory or design of the invention or of the scope afforded in construing the claims, it is believed that the combination of the oxidizing and non-oxidizing biocides creates an equilibrium that creates a persistently hostile environment in the pipeline for microorganisms. Specifically the first oxidizing treatment eliminates much of the microorganisms. Its combination with the non-oxidizing biocide drastically reduces the oxidative potential of the oxidizing biocide (possibly by reduction). This results in two benefits. First it reacts much more slowly and persists through a long length of the pipeline. Second its lower activity makes it less likely or not likely at all to corrode the pipeline. While the reduced activity oxidizing biocide might not have been effective on the original microorganism population present in the original fluid source, because it has some time to operate on those microorganisms before the addition of the reducing biocide, the only remaining population in the pipeline is a small number of survivors that the low activity oxidizing biocide can more than handle. In addition the less active oxidizing biocide will react less with the inorganic materials prevalent in the pipeline and therefore can make use of the prolonged contact time with the microorganisms to eliminate them. Thus the invention is especially suited to the specific conditions in a slurry transport pipeline. Potentially any microorganism that is resistant to oxidizing biocide is unlikely to be resistant to non-oxidizing biocide. Thus it is a good strategy use two kinds of biocides in one system.

In at least one embodiment in addition to the biocide(s), also added to the pipeline is a corrosion inhibitor. Representative examples of corrosion inhibitors include but are not limited to those described in U.S. Pat. No. 8,557,338. In at least one embodiment but for its reaction with the reducing biocide, the oxidizing biocide would have impaired and/or completely disabled the corrosion inhibitor, but instead the biocide does not (or does less) inhibit the effectiveness of the corrosion inhibitor.

In at least one embodiment the corrosion inhibitor is a composition comprising: at least 60% water, 1-20% zinc compound and 1-20% phosphoric acid or phosphate compounds or any phosphorous compound, and/or it may comprise an oxygen scavenger including but not limited to sodium bisulfate. Representative zinc compounds include but are not limited to zinc chloride, zinc oxide, zinc sulfate, zinc phosphate, and the like, and any combination thereof.

In at least one embodiment the corrosion inhibitor is a composition comprising at least one of: methoxypropylamine and monoethanolamine. In an embodiment, the corrosion inhibitor of the invention comprises a product of dimethylaminoethoxyethanol, dimethylethanolamine, tall oil, C18-unsaturated fatty acid trimers, and branched dodecylbenzenesulfonic acid (DDBSA).

In another embodiment, the corrosion inhibitor of the invention comprises a product of tall oil, reaction products with 2-[2-(dimethylamino)ethoxy]ethanol, 2-(dimethylamino)ethanol, C18-unsaturated fatty acid trimers, and branched DDBSA.

Representative alkanolamines include N,N-dimethylethanolamines, such as (N,N-dimethylaminoethoxy)ethanol;

dimethylethanolamine; triethanolamine; methyldiethanolamine; ethanolamine; diethanolamine; other cyclic amines including morpholine, methylmorpholine, ethylmorpholine, piperidine, alkylpiperidines, piperazine, alkylpiperazines; ethyleneamines including DETA, TETA, TEPA, and the like; alkylamines including methylamine, dimethylamine, alkylmethylamines, dimethylalkylamines; methylaminopropylamine; dimethylaminopropylamine; dimethylaminoethylamine; methylaminoethylamine; the like; and combinations thereof.

Representative fatty acids include trimeric C18 unsaturated fatty acid (e.g., CAS 68937-90-6), dimer acids, polymerized tall-oil fatty acids, one or more components of a crude tall oil composition, branched DDBSA, the like, and any combination of the foregoing. For example, a crude tall oil composition may include abietic acid; neoabietic acid; palustric acid; pimaric acid; dehydroabietic acid; palmitic acid; stearic acid; palmitoleic acid; linoleic acid; 5,9,12-octadecatrienoic acid; linolenic acid; 5,11,14-eicosadienoic acid; cis,cis-5,9-octadecadienoic acid; eicosadienoic acid; elaidic acid; cis-1,1-octadecanoic acid, C20-C24 saturated acids; the like; and any combination of the foregoing.

In an embodiment, the corrosion inhibitor composition of the invention includes the following formula (1) using dimethylalkanolamines with trimer acid [CAS 68937-90-6].

The above formulas (1) and (2), the representative acyclic trimer acid/amine salts which may be formed, for example, in the blending of trimer acid and a mixture of select alkanolamines. For simplicity of weight percentage composition, it has been assumed that the di- and tri-salts formed from two and three equivalents of amine, respectively, versus a single trimer molecule is negligible. Due to the complex mixture of species in trimer acid (i.e., cyclic trimers, aromatic trimers, polycyclic trimers, cyclic dimers, aromatic dimers, polycyclic dimers, and numerous isomeric species of the aforementioned chemicals) a representative acyclic structure of the acid is used. In addition, trimer acid contains variable percentages of dimers and trimers, adding to the complexity. A typical composition can include approximately 40% dimer and 60% trimer with insignificant percentages of the monomer.

In an embodiment, the corrosion inhibitor composition of the invention includes the following formula (3) using dimethylalkanolamines with tall oil [CAS 8002-26-4].

(3)

(1)

In an embodiment, the corrosion inhibitor composition of the invention includes the following formula (2) dimethylalkanolamines with trimer acid [CAS 68937-90-6].

(2)

In an embodiment, the corrosion inhibitor composition of the invention includes the following formula (4) using dimethylalkanolamines with tall oil [CAS 8002-26-4].

(4)

The second group of salts which can form in this blend is with tall oil, exemplified in formulas (3) and (4) above. Crude tall oil is, for example, a by-product of the pulp and paper industry and yields another complex mixture of fatty acids, rosin acids, and lesser amounts of terpenes and sterols. The composition of tall oil is variable with differences seen in regional sources and manufacturing processes as well as seasonal influences. Crude tall oil and distilled tall oil can also be very different. These differences are well known in the art. The structures above provide a representation of the salts formed from dimethylalkanolamines and tall oil (oleic acid is shown).

The structures below provide representative examples of the various acids present in this mixture:

abietic acid neoabietic acid palustric acid pimaric acid dehydroabietic acid

Palmitic acid

Palmitoleic acid

Stearic acid

Linoleic acid

Other representative tall oil fatty acids include 5,9,12-octadecatrienoic acid; linolenic acid; 5,11,14-eicosatrenoic acid; cis,cis-5,9-octadecadienoic acid; eicosadienoic acid; elaidic acid; cis-11-octadecanoic acid; and C20, C22, C24 saturated acids. Tall oil fatty acids may comprise any combination of the foregoing examples and others known in the art.

In an embodiment, the corrosion inhibitor composition of the invention includes the following formula (5) using dimethylalkanolamines with branched dodecylbenzene sulfonic acid [CAS 68411-32-5].

(5)

In an embodiment, the corrosion inhibitor composition of the invention includes the following formula (6) using dimethylalkanolamines with branched dodecylbenzene sulfonic acid [CAS 68411-32-5].

(6)

A representative structure of the salts formed with branched dodecylbenzene sulfonic acid (DDBSA) is shown above. The composition of these salts has been approximated based on general reactivity and percentages of each acid added to the blends.

In an embodiment, the product of the invention comprises about 10 wt % to about 100 wt % active ingredient. In another embodiment, the amount of active is from about 10 wt % to about 36 wt %. Preferably, the amount ranges from about 15 wt % to about 30 wt % active. In one embodiment, the product comprises about 27 wt % of the active.

In an embodiment, the corrosion inhibitor composition of the invention may include at least one solvent. Representative solvents include methanol, ethanol, propanol, isopropanol, butanol, isobutanol, aromatic hydrocarbons, isoparaffinic solvents, monoethyleneglycol, ethylene glycol monobutyl ether, the like, water (water can also be used to emulsify the corrosion inhibitor), and combinations thereof. A solvent component aids in corrosion inhibitor delivery and helps provide desirable secondary properties of the product, such as desired viscosity, temperature stability, and the like. In embodiments, the amount of solvent may range from about 8.5 wt % to about 90 wt %. In other embodiments, the amount of solvent may range from about 30 wt % to about 40 wt %.

In an embodiment, the corrosion inhibitor composition of the invention may include at least one dispersant. The dispersant is preferably an oxyalkylate polymer (i.e., polyoxyethylene) such as ethoxylated sorbitan monolaurate. This may include varying oxyalkylated sorbitan esters (e.g., mono, di-, and tri-esters) and non-oxyalkylated sorbitan esters as well. In embodiments, the amount of polyoxyalkylate can vary from about 1-2 mol % up to about 80 mol %, preferably 20 mol %. In embodiments, the amount of oxyalkylated sorbitan esters in the final product ranges from about 1 wt % to about 10 wt %, preferred about 1 wt % to about 5 wt %.

In another embodiment, the corrosion inhibitor composition of the invention further comprises at least one quaternary ammonium compound in the range of about 5-35 wt %, preferred about 5-20 wt %.

In another embodiment, the corrosion inhibitor composition of the invention includes at least one solvent and at least one dispersant.

In at least one embodiment the microbiological activity of the fluid is measured by a suitable device located at one or more points before, along, or downstream from the pipeline. Representative examples of such devices include those described in U.S. Pat. Nos. 8,012,758, 7,981,679, 7,949,432, 8,613,837, and U.S. patent application Ser. Nos. 14/138,526 and 13/657,993. In at least one embodiment the feed mechanism of one or more of the biocides and/or corrosion inhibitors is at least partially automated and controlled by process logic which evaluates the measurements from a suitable device and appropriately feeds, ceases feeding, and/or adjusts feed amounts, rates, dosages, and/or concentrations accordingly.

In at least one embodiment the pH of the media is adjusted to values between 10.0 and 4.0, more preferably between 5.0 and 8.0 and even more preferably between 6.0 and 7.5. The pH adjustment can be carried out in any practical manner including but not limited to one or more metal hydroxide, and/or a carbonate or a bicarbonate of any metal including but not limited to calcium, sodium, potassium, and any combination thereof. pH adjustment may also be achieved by using any molecule with alkaline or basic (non-acidic) characteristics like ammonia, amines and hydroxyl compounds alone or in any combination of the aforementioned. Representative examples of pH adjustors include but are not limited to sodium hydroxide, sodium carbonate, calcium hydroxide, and any combination thereof.

The invention has the advantage of allowing for the construction and continuous use of pipelines with cheaper materials than biocorrosion resistant steels. It also eliminates the need of coating mild steel pipelines built for ore slurry transport and it can be used in existing pipelines as mild steel pipelines. The invention allows for the use of strong oxidizing biocides to treat the water pumped in a mild steel pipeline which, along with the use of non-oxidizing biocide, guarantees good microbiological control, no corrosion issues and lower total biocide consumption.

EXAMPLES

The foregoing may be better understood by reference to the following examples, which are presented for purposes of illustration and are not intended to limit the scope of the invention. In particular the examples demonstrate representative examples of principles innate to the invention and these principles are not strictly limited to the specific condition recited in these examples. As a result it should be understood that the invention encompasses various changes and modifications to the examples described herein and such changes and modifications can be made without departing from the spirit and scope of the invention and without diminishing its intended advantages. It is therefore intended that such changes and modifications be covered by the appended claims.

Example 1—Microbiological Efficiency of Treatment with Oxidizing Biocide Compared to Non-Oxidizing Biocide Two water samples collected directly of makeup water of a pipeline sourced form river water, were submitted to biocide treatment. One sample was highly contaminated with microorganisms (1700 CFU/mL) while the other was less contaminated (120 CFU/mL). The efficiency of treatment with oxidizing-biocide was superior in case on highly contaminated water (Test 3) while both treatments showed a satisfactory performance in case of less contaminated sample as showed in Table 1. There is a dramatic reduction in required dosage using oxidizing biocide ($Cl_2O$) (Tests 3, 4 and 7).

TABLE 1

Microbiological efficiency of treatment with oxidizing biocide compared to non-oxidizing biocide only.

| Test | Initial Count Total Aerobic Bacteria (CFU/mL) | Initial Count Sulfate Reducing Bacteria (CFU/mL) | Biocide | Dosage (ppm) | Final Count Total Aerobic Bacteria (CFU/mL) | Final Count Sulfate Reducing Bacteria (CFU/mL) |
|---|---|---|---|---|---|---|
| 1 | 1700 | 30 | A | 500 | 330 | 10 |
| 2 | 1700 | 30 | B | 350 | 350 | <10 |
| 3 | 1700 | 30 | $ClO_2$ | 5 | 30 | <10 |
| 4 | 120 | <10 | $ClO_2$ | 4 | <27 | <10 |
| 5 | 120 | <10 | A | 500 | <27 | <10 |
| 6 | 120 | <10 | B | 350 | <27 | <10 |
| 7 | 120 | <10 | $ClO_2$ | 1.5 | <27 | <10 |

A - Glutaraldehyde
B - Sodium dimethyldithiocarbamate + Disodium ethylenebis(dithiocarbamate)

Example 2—Corrosion Rate Increase Due Presence of Oxidizing Biocide $Cl_2O$

Tests were carried out using makeup water from a pipeline operator using river water that had not had any previous treatment. Tubular coupons made of C1018 mild carbon steel were used for the weight loss measurements. Coupons dimensions were: outside Some experiments had its pH adjusted using lime ($Ca(OH)_2$).

Weight Loss Balance Experiments

An acceptable way to follow corrosion rate is through mass loss balance. This technique is suitable for both generalized and localized corrosion and can be described as follows. The tubular coupons received a surface treatment after each electrochemical experiment in order to remove any corrosion product eventually deposited on the surface before being weighted. The electrodes were copiously rinsed with taped water, smoothly brushed and then immersed into concentrated hydrochloric acid for 5 seconds. Finally, the electrodes were copiously rinsed with distilled water, dried and weighted.

$$W = w_1 - w_2 \quad (5)$$

where: W: total weight loss
$w_1$: pre-test weight
$w_2$: post-test weight

Corrosion rate can be obtained according the equation (6):

$$\text{corrosion rate} = \frac{W}{\rho * A * t}$$

where: $\rho$ = mild steel density
A = surface area
t = experiment time

Once corrosion rate (CR) is known for a specific sample of water, corrosion inhibitor performance could be evaluated. Measurement of weight loss was carried out keeping the coupon rotation at specific speed. This assay is carried out in same conditions of first test but this time in presence of corrosion inhibitor. The percent protection relative to blank samples can be determined for each chemical according to the following equation:

Efficiency of inhibition (%) = ((CR − $CR_{CI}$) × 100)/CR where, CR is the corrosion rate without any treatment and $CR_{CI}$ is the corrosion rate determined in the presence of corrosion inhibitor.

Surface Examination

Diagnosis between localized and general corrosion can be accomplished through surface examination before and after each trial. This exam was recorded using regular digital camera and microscopy with 40× or 100× magnification lens. This qualitative method is extremely useful to evaluate the performance of corrosion inhibitor especially when localized corrosion or pitting is taking place.

Comparison between corrosion rate obtains in crude water, water with corrosion inhibitor and influence of oxidizing biocide is showed in Table 2. Corrosion inhibitor composition in this case was based on zinc compounds and phosphate compounds.

TABLE 2

Comparison between corrosion rates obtained in crude water and with corrosion inhibitor and influence of oxidizing biocide

| Test | Corrosion inhibitor dosage (ppm) | $Cl_2O$ Dosage (ppm) | pH* | Corrosion rate (mpy) |
|---|---|---|---|---|
| 8** | — | — | 5.02 | 17.8 |
| 9 | 60 | — | 6.90 | 7.3 |
| 10 | — | 30 | 7.09 | 63 |
| 11 | 60 | 30 | 7.06 | 29 |
| 12 | 120 | 30 | 7.05 | 19 |
| 13 | 60 | 3.9 | 7.01 | 13 |

*pH adjustment carried out using calcium hydroxide
**Blank trial, untreated, crude water As can be observed in Test 8 the untreated water is corrosive to mild steel. The use of corrosion inhibitor can reduce this effect (Test 9) but the presence of oxidizing biocide (Test 10 and 11) even at lower dosage (Test 13) increases the corrosion rate. Corrosion inhibitor in these cases, even at higher dosages (Trial 12), cannot sufficiently protect the mild steel against corrosion.

Figure 1:
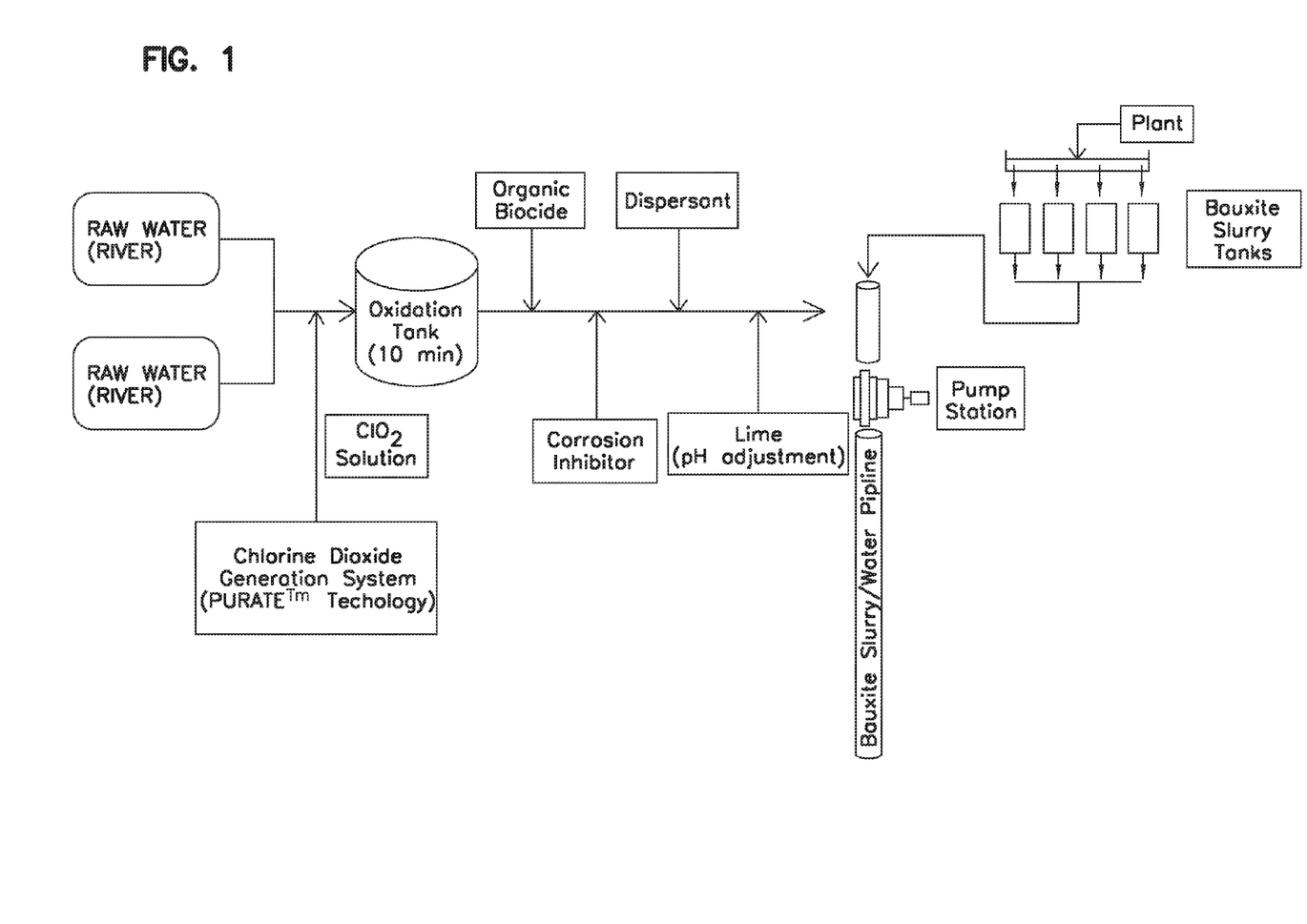
FIG. 1 is an illustration of a slurry pipeline within which the invention is applied.
Figure 2:
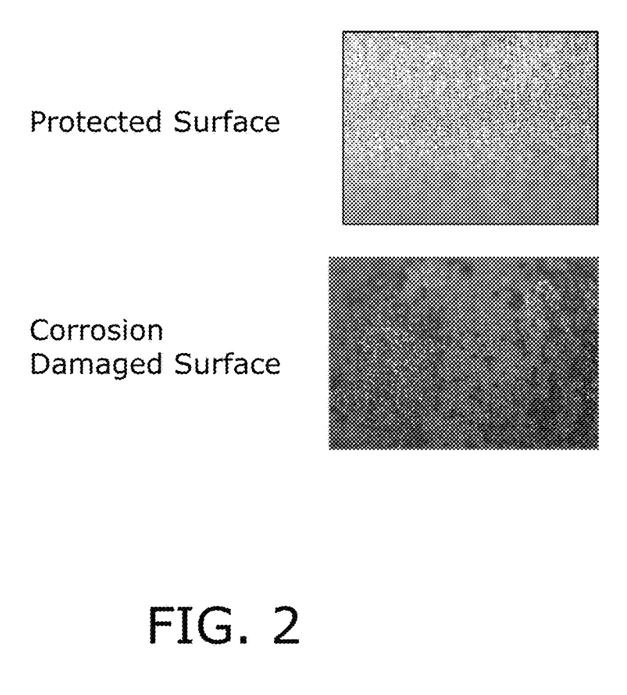
FIG. 2 is microscopy pictures (40× magnification) showing differences between a still polished-protected surface (top) and a coarse surface damaged by corrosion (bottom).

It is also important to analyze the final aspect of the metallic surface at the end of the trials. Microscopy pictures (40× magnification) showed significant damage to the metallic surface and localized corrosion when oxidizing biocide was used. FIG. 2 illustrates the differences between a protected surface (Test 9) and a corrosion damaged surface (Test 10).

Example 3—Effect of Combined Oxidizing Biocide $Cl_2O$ and Non-Oxidizing Biocide Over Corrosion Rate in Presence of Corrosion Inhibitor The presence of oxidizing biocide may be beneficial from the perspective of microbiological control (Table 1) but is clearly detrimental from the perspective of corrosion rate (Table 2). The use of non-oxidizing biocide working at the same time as a reductive agent, neutralizing the oxidizing biocide and preventing any further contamination, can represent an important advantage in the strategy of microbiological control and corrosion control. Table 3 shows the results obtained for corrosion rate of mild steel using oxidizing biocide followed by a non-oxidizing biocide. Each water sample was treated with chlorine dioxide for ten minutes and then treated with non-oxidizing biocide, corrosion inhibitor and lime (calcium hydroxide) for pH adjustments.

TABLE 3

Effect of combined oxidizing biocide Cl2O and non-oxidizing biocide over corrosion rate in presence of corrosion inhibitor and dispersant.

| Test | $Cl_2O$ Dosage (ppm) | Non-oxidizing biocide (ppm)* | Corrosion inhibitor dosage (ppm) | Dispersant (ppm) | pH** | Corrosion rate (mpy) |
|---|---|---|---|---|---|---|
| 14 | 4 | 50 | 60 | 33.4 | 6.96 | 5.7 |
| 15 | 4 | 100 | 60 | 33.4 | 7.18 | 4.3 |
| 16 | 4 | 50 | 60 | — | 6.12 | 7.2 |
| 17 | 4 | 50 | 60 | 16.7 | 6.01 | 3.6 |
| 18 | 4 | 50 | 60 | 16.7 | 5.00 | 4.5 |
| 19 | 4 | 50 | 60 | — | 5.02 | 4.3 |

*Non oxidizing biocide is Sodium dimethyldithiocarbamate + Disodium ethylenebis (dithiocarbamate) (50 ppm) or Glutaraldehyde (100 ppm)
**pH adjustment with calcium hydroxide Results showed in Table 3 clearly demonstrate that the corrosion rate is under control when non-oxidizing biocide is dosed after oxidizing biocide in presence of corrosion inhibitor. All values obtained for corrosion rate are lower than observed in previous examples (Table 2, Tests 10 to 13) when oxidizing biocide was applied in absence of non-oxidizing biocide even in the presence or corrosion inhibitor. Moreover, all values obtained for corrosion rate are lower than the original value observed when just water and corrosion inhibitor were mixed (Table 2, Test 9) indicating the benefit of using non-oxidizing biocide. Tests 14 to 19 also demonstrate that this technology can be used in presence of a dispersant and in a broad pH range.

Figure 3:
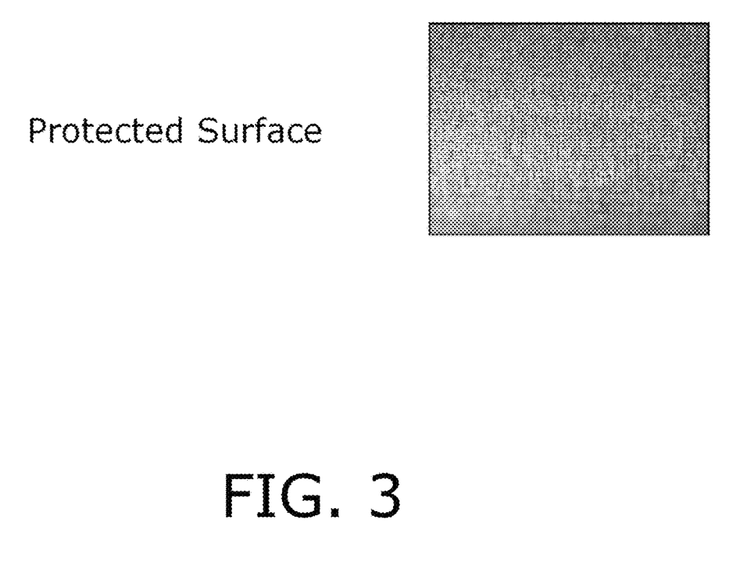
FIG. 3 is a microscopy picture (40× magnification) showing the aspect of a protected surface at the end of a corrosion evaluation trial (Test 14).

It is also important notice the final aspect of the metallic surface that showed no signs of attack. At the end of these trials the metallic surface was still smooth and polished as it was at the beginning of the trials. FIG. 3 shows one example.

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein or mentioned therein are incorporated by reference in their entirety. Furthermore, the invention encompasses any possible combination of some or all of the various embodiments mentioned herein, described herein and/or incorporated herein. In addition the invention encompasses any possible combination that also specifically excludes any one or some of the various embodiments mentioned herein, described herein and/or incorporated herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range. All percentages, ratios and proportions herein are by weight unless otherwise specified.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method of reducing the presence of microorganisms in a pipeline, the method comprising the following steps in order:
    applying a fluid comprising microorganisms to an oxidizing tank;
    adding an oxidizing biocide to the fluid in an amount higher than the oxidant demand of the pipeline, wherein the oxidizing biocide is selected from: chlorine dioxide; chlorine gas; hypochlorous acid; and a reaction product of metal chlorate, hydrogen peroxide, and an acid, wherein the acid is selected from mineral acid, chlorous acid, or a combination thereof;
    allowing a period of time to pass so that the oxidizing biocide eliminates substantially all of the microorganisms in the fluid;
    adding a non-oxidizing biocide to the fluid in an amount less than 30% of the minimum necessary to sterilize the microorganisms in the absence of the oxidizing biocide, and wherein the amount of non-oxidizing biocide is in an amount sufficient to neutralize the oxidizing biocide; and
    feeding the fluid into the pipeline.
2. The method of claim 1 wherein the fluid is a plug.
3. The method of claim 1 wherein the fluid is seawater.
4. The method of claim 1 further comprising adding a corrosion inhibitor to the fluid, wherein the corrosion inhibitor is rendered ineffective by the oxidizing biocide in the absence of the non-oxidizing biocide.

5. The method of claim 4 wherein the pipeline suffers no more corrosion-erosion than the same pipeline in the absence of the oxidizing biocide and/or the non-oxidizing biocide.

6. The method of claim 4 wherein the corrosion inhibitor is added to the fluid contemporaneously with the non-oxidizing biocide.

7. The method of claim 4 wherein the corrosion inhibitor is added to the fluid after the addition of the non-oxidizing biocide.

8. The method of claim 4 wherein the corrosion inhibitor comprises a zinc compound and phosphorus compound.

9. The method of claim 4 wherein the corrosion inhibitor comprises sodium bisulfite.

10. The method of claim 4 wherein the corrosion inhibitor comprises methoxypropylamine, monoethanolamine, or a combination thereof.

11. The method of claim 4 wherein the corrosion inhibitor comprises a product of dimethylaminoethoxyethanol, dimethylethanolamine, tall oil, C18-unsaturated fatty acid trimers, and branched dodecylbenzenesulfonic acid.

12. The method of claim 4 wherein the corrosion inhibitor comprises a reaction product of tall oil with 2[2-(dimethylamino)ethoxy]ethanol, 2-(dimethylyamin)ethanol, C18-unsaturated fatty acid trimers, and branched dodecylbenzenesulfonic acid.

13. The method of claim 1 wherein the at least a portion of the pipeline in contact with the fluid is constructed essentially out of mild steel and the presence of the oxidizing biocide reduces biocorrosion and substantially does not cause corrosion.

14. The method of claim 13 in which the dosage of the biocides are such that it reduces biocorrosion at the distal end of the pipeline while substantially not increasing corrosion at the proximal end of the pipeline.

15. The method of claim 1 in which the dosage of oxidizing biocide to the fluid is 1-10 ppm and the dosage of non-oxidizing biocide to the fluid is 1-200 ppm.

16. The method of claim 1 in which a majority of the pipeline in contact with the fluid is constructed essentially out of mild steel and the presence of the oxidizing biocide reduces biocorrosion and does not cause corrosion.

17. The method of claim 1 in which the dosage of oxidizing biocide to the fluid is 1-10 ppm and the dosage of non-oxidizing biocide to the fluid is 50-120 ppm.

18. The method of claim 1 wherein the period of time is about 10 minutes.

* * * * *